United States Patent
Darimont-Nicolau et al.

(10) Patent No.: US 9,962,415 B2
(45) Date of Patent: May 8, 2018

(54) LACHNOSPIRACEAE IN THE GUT MICROBIOTA AND ASSOCIATION WITH BODY WEIGHT

(71) Applicant: NESTEC S.A., Vevey (CH)

(72) Inventors: Christian Darimont-Nicolau, Lausanne (CH); Bernard Berger, Chatillens (CH); Enea Rezzonico, Epalinges (CH); Catherine Ngom-Bru, Montpreveyres (CH); Melissa LePage, Savigny (CH)

(73) Assignee: Nestec S.A., Vevey (CH)

( * ) Notice: Subject to any disclaimer, the term of this patent is extended or adjusted under 35 U.S.C. 154(b) by 3 days.

(21) Appl. No.: 14/787,817

(22) PCT Filed: May 1, 2014

(86) PCT No.: PCT/EP2014/058942
§ 371 (c)(1),
(2) Date: Oct. 29, 2015

(87) PCT Pub. No.: WO2014/177667
PCT Pub. Date: Nov. 6, 2014

(65) Prior Publication Data
US 2016/0089404 A1    Mar. 31, 2016

(30) Foreign Application Priority Data
May 3, 2013 (EP) .................................... 13166562

(51) Int. Cl.
| | | |
|---|---|---|
| A01N 63/00 | (2006.01) | |
| A61K 35/747 | (2015.01) | |
| A61K 8/99 | (2017.01) | |
| C12Q 1/04 | (2006.01) | |
| A61Q 19/06 | (2006.01) | |
| C12Q 1/06 | (2006.01) | |
| A23L 33/135 | (2016.01) | |

(52) U.S. Cl.
CPC .......... *A61K 35/747* (2013.01); *A23L 33/135* (2016.08); *A61K 8/99* (2013.01); *A61Q 19/06* (2013.01); *C12Q 1/04* (2013.01); *C12Q 1/06* (2013.01); *A23V 2002/00* (2013.01); *A23Y 2220/73* (2013.01); *A61K 2800/92* (2013.01); *G01N 2333/33* (2013.01); *G01N 2800/044* (2013.01)

(58) Field of Classification Search
None
See application file for complete search history.

(56) References Cited

U.S. PATENT DOCUMENTS

| | | |
|---|---|---|
| 7,001,756 B1 | 2/2006 | Hsu et al. |
| 2005/0186189 A1 | 8/2005 | Hsu et al. |
| 2010/0172874 A1 | 7/2010 | Turnbaugh et al. |
| 2012/0058094 A1 | 3/2012 | Blaser et al. |

FOREIGN PATENT DOCUMENTS

| | | |
|---|---|---|
| CN | 1670183 | 9/2005 |
| EP | 2022502 | 2/2009 |
| EP | 2030623 | 3/2009 |
| WO | 2006019222 | 2/2006 |
| WO | 2009021824 | 2/2009 |
| WO | 2009024429 | 2/2009 |
| WO | 2012131099 | 10/2012 |

OTHER PUBLICATIONS

De La Serre et al., Am J Physiol., Gasterointest. Liver Physiol., 2010, vol. 299, No. 2, p. G440-G448.*
Ravussin et al. "Responses of Gut Microbiota to Diet Composition and Weight Loss in Lean and Obese Mice" Obesity, 2012, vol. 20, pp. 738-747, XP000917110.
Harris et al. "Is the Gut Microbiota a New Factor Contributing to Obesity and Its Metabolic Disorders?" Journal of Obesity, vol. 2012, article ID 879151, 14 pages, XP055070564.

* cited by examiner

*Primary Examiner* — Kade Ariani
(74) *Attorney, Agent, or Firm* — K&L Gates LLP

(57) ABSTRACT

The present invention relates to means and methods for modulating the gut microbiota composition of a subject, preferably a human. In particular, the present invention provides an agent capable of reducing the proportion of Lachnospiraceae in the gut microbiota composition of a subject which agent is useful for promoting weight loss or preventing weight gain in a subject, preferably an obese or overweight subject. *Lactobacillus rhamnosus* CGMCC 1.3724 is particularly preferred as the agent provided by and used in the present invention.

11 Claims, 3 Drawing Sheets

LACHNOSPIRACEAE IN THE GUT MICROBIOTA AND ASSOCIATION WITH BODY WEIGHT

CROSS REFERENCE TO RELATED APPLICATIONS

The present application is a National Stage of International Application No. PCT/EP2014/058942, filed on May 1, 2014, which claims priority to European Patent Application No. 13166562.2, filed on May 3, 2013, the entire contents of which are being incorporated herein by reference.

The present invention relates to means and methods for modulating the gut microbiota composition of a subject, preferably a human. More particularly, the present invention relates to probiotics for reducing the proportion of bacteria from the Lachnospiraceae family in said gut microbiota composition. In particular, the present invention relates to reducing said Lachnospiraceae proportion for promoting body weight loss.

BACKGROUND OF THE INVENTION

The prevalence of obesity has grown in an alarming rate in the past 20 years. Based on an estimate in 2004, in the US alone, 66.3% of adults are either overweight or obese, and 32.2% of adults are classified as obese (Cynthia L. Ogden et al., JAMA 2006 Apr. 5; 295:1549-1555). Both genetic and environmental factors have been shown to cause positive energy balance and obesity. Obesity by itself is only a part of problems. Many other chronic diseases such as type 2 diabetes, certain cancers and cardiovascular diseases are common co-morbidities of obesity. Collectively, all the obesity associated medical issues put a tremendous amounts of pressure on health care systems in many countries.

Drug treatments for obesity are available but not very effective and with undesirable side-effects. Still more drugs are under development to improve the safety, efficacy of the medications and convenience to use them by patients. To date, all anti-obesity treatments are designed to alter the internal metabolism of patients. Most of these drugs are required to be absorbed and delivered to target organs through blood stream for their efficacy. Safety concerns of such a treatment strategy cannot be ignored.

Novel treatment strategies of obesity and type 2 diabetes focussing on targets outside of human tissues is greatly desirable because the active agents are not required to enter our body, and the safety of the treatments can be improved significantly.

Recent research has shown that gut bacteria play a role in the development of obesity and related metabolic disorders such as diabetes (Kristina Harris, et al., Journal of Obesity 2012; 2012:879151; doi:10.1155/2012/879151). Human beings are superorganisms with a body composed of millions of human cells while many more bacteria live, e.g., in the colon. It has been estimated that more than $10^{13}$ to $10^{14}$ bacteria are alive in a healthy human intestine. Intestinal bacteria can be separated into 2 major divisions, *Firmicutes* and *Bacteriodetes* (Steven R. Gill, et al., Science 2006 Jun. 2; 312:1355-1359; Peter J. Turnbaugh, et al., Nature 2006 Dec. 21; 444:1027-131). Together, they represent at least 90% of total bacterial population in the gut. The presence of the gut bacteria is a part of normal human physiology and is important for the development of gut functions (Hooper L V et al., Science. 2001 Feb. 2; 291(5505):881-4; Stappenbeck T S, et al., Proc Natl Acad Sci USA. 2002 Nov. 26; 99(24):15451-5), maturation of the immune system (Mazmanian S K, et al., Cell. 2005 Jul. 15; 122(1):107-18), harvesting energy from dietary carbohydrates (Peter J. Turnbaugh, et al., Nature 2006 Dec. 21; 444:1027-131), harvesting essential vitamins (Backhed F, et al., Science. 2005 Mar. 25; 307(5717):1915-20) and metabolizing environmental chemicals in the gut (Nicholson J K, et al., Nat Rev Microbiol. 2005 May; 3(5):431-8). Recent studies further suggested that gut bacteria may be involved in fat storage (Backhed F, et al., Proc Natl Acad Sci USA. 2004 Nov. 2; 101(44):15718-23).

WO 2006/019222 discloses *Lactobacillus rhamnosus* strain PL60 KCCM-10654P with a body-fat reducing activity that overproduces t10c12-octadecadienoic acid.

U.S. Pat. No. 7,001,756 and CN1670183 provide an isolated microorganism strain *Lactobacillus rhamnosus* GM-020 which is found to be effective in treating obesity.

WO 2009/0218424 describes a composition comprising *Lactobacillus rhamnosus* strain CGMCC 1.3724 or NCC4007 which is useful for supporting weight loss or weight management.

WO 2009/024429 describes a similar composition comprising *Lactobacillus rhamnosus* strain CGMCC 1.3724 or NCC4007 for the use in treating or preventing metabolic disorders. The composition was shown to modify the amount of *Proteobacteria* in the gut. Optimum results were achieved when the ratio of *Proteobacteria* to *Bacteriodetes* was reduced. At the same time, the ratio of *Proteobacteria* to *Firmicutes* and/or the ratio of *Bacteriodetes* to *Firmicutes* may be increased.

However, further elucidation of the relationship between gut microbiota and body weight is required in order to provide a solid basis for the development of effective and safe strategies for body weight management.

It was one thus an object of the present invention to improve the management of body weight and, in this context, the treatment of obesity and overweight by modulating the population of gut bacteria.

SUMMARY OF THE INVENTION

The aim of the present invention is achieved by subject-matter as specified in the independent claims. Particular embodiments of the invention are as specified in the dependent claims.

The object of the present invention is solved by an agent capable of reducing the proportion of Lachnospiraceae in the gut microbiota composition of a subject for use in promoting weight loss in an obese or overweight subject.

In one embodiment, the agent is for use in promoting weight loss during, subsequent to and/or prior to a calorie restricted diet.

The object is further solved by an agent capable of reducing the proportion of Lachnospiraceae in the gut microbiota composition of a subject for use in preventing weight gain in an obese or overweight subject, or for preventing weight regain in a previously obese or overweight subject.

In one embodiment, the agent is for use in preventing weight gain or weight regain subsequent to a calorie restricted diet.

The object is further solved by the use of an agent capable of reducing the proportion of Lachnospiraceae in the gut microbiota composition of a subject for the preparation of a pharmaceutical composition for promoting weight loss in an obese or overweight subject.

In one embodiment, the pharmaceutical composition comprising the agent is for promoting weight loss during, subsequent to and/or prior to a calorie restricted diet.

The object is further solved by the use of an agent capable of reducing the proportion of Lachnospiraceae in the gut microbiota composition of a subject, for the preparation of a pharmaceutical composition for preventing weight gain in an obese or overweight subject or weight regain in a previously obese or overweight subject.

In one embodiment, the pharmaceutical composition comprising the agent is for preventing weight gain or weight regain subsequent to a calorie restricted diet.

The object is further solved by a method for promoting weight loss in an obese or overweight subject, the method comprising administering to the subject an effective amount of an agent capable of reducing the proportion of Lachnospiraceae in the gut microbiota composition of the subject.

In one embodiment, the method for promoting weight loss is used during, subsequent to and/or prior to a calorie restricted diet.

The object is further solved by a method for preventing weight gain in an obese or overweight subject, or for preventing weight regain in a previously obese or overweight subject, the method comprising administering to the subject an effective amount of an agent capable of reducing the proportion of Lachnospiraceae proportion in the gut microbiota composition of a subject.

In one embodiment, the method for preventing weight gain or weight regain is used subsequent to a calorie restricted diet.

The object is further solved by use of an agent capable of reducing the proportion of Lachnospiraceae in the gut microbiota composition of a subject for promoting weight loss or preventing weight gain in a normal weight subject.

In one embodiment, the agent is used during, subsequent to and/or prior to a calorie restricted diet.

In one embodiment of the present invention, the weight loss involves or is due to a body fat loss. Similarly, the weight gain involves or is due to a body fat gain, or the weight regain involves or is due to a body fat gain.

In one embodiment of the present invention, the agent is selected from the group consisting of probiotics, preferably is selected from the group consisting of probiotic *Lactobacillus rhamnosus* strains, most preferably is *Lactobacillus rhamnosus* strain CGMCC 1.3724, also referred to as *Lactobacillus rhamnosus* strain NCC4007.

In one embodiment of the present invention, a *Lactobacillus rhamnosus* strain is administered to the subject at a daily dosage in the range of $10^2$ to $10^{12}$ cfu, preferably at a daily dosage in the range of $10^6$ to $10^{10}$, more preferably at a daily dosage in the range of $10^7$ to $10^9$ cfu.

In a particularly preferred embodiment, *Lactobacillus rhamnosus* strain CGMCC 1.3724 is administered to the subject at a daily dosage of $3.2 \times 10^8$ cfu. In an even more preferred embodiment, the daily dosage is administered in the form of two sub-dosages of $1.6 \times 10^8$ cfu each.

In one embodiment of the present invention, the calorie restricted diet involves a reduction of the daily calorie intake in the range of 200 to 1000 kcal, preferably in the range of 400 to 750 kcal, more preferably by at least 500 kcal.

In one embodiment of the present invention, the agent is used or administered to the subject over a period of at least 6 weeks, preferably over a period of at least 12 weeks, more preferably over a period of at least 24 weeks, most preferably of at least 36 weeks.

In one embodiment of the present invention, the agent is used or administered to the subject over a calorie restriction period, also referred to as weight loss period, and over a subsequent period without calorie restriction, also referred to as weight maintenance period.

In a particularly preferred embodiment, the agent is used or administered to the subject over a calorie restriction period, also referred to as weight loss period, of at least 12 weeks, and over a subsequent period without calorie restriction, also referred to as weight maintenance period of at least further 12 weeks.

In one embodiment of the present invention, the agent is capable of reducing the proportion of Lachnospiraceae in the gut microbiota composition of a subject by at least 5%, more preferably by at least 10%, most preferably by at least 15%, compared to the initial proportion of Lachnospiraceae in the gut microbiota of the subject before the administration of the agent.

The object of the present invention is further solved by a method for identifying an agent capable of reducing the proportion of Lachnospiraceae in the gut microbiota composition of a subject, said method comprising the steps of:
  (a) determining the proportion of Lachnospiraceae in the gut (fecal) microbiota composition of a test subject;
  (b) administering to the test subject a candidate agent over a period of time;
  (c) re-determining after said period of time the proportion of Lachnospiraceae in the gut microbiota composition of the test subject;
  (d) comparing the results of steps (a) and (c); and
  (e) qualifying a candidate agent reducing the proportion of Lachnospiraceae by at least 5% in the test subject, more preferably by at least 10%, most preferably by at least 15% as an agent capable of reducing the proportion of Lachnospiraceae in the gut microbiota composition of a subject.

The object of the present invention is further solved by a method for diagnosing an obesity being dependent on the gut microbiota composition, said method comprising the steps of:
  (a) determining ex vivo the proportion of Lachnospiraceae in the gut (fecal) microbiota composition of a subject;
  (b) comparing the result of step (a) to a reference, preferably a reference derived from normal weight subject;
  (c) diagnosing obesity depending on the gut microbiota composition when the result of step (a) exceeds the reference by at least 5%, more preferably by at least 10%, most preferably by at least 15%.

The object of the present invention is further solved by a method for diagnosing a low responsiveness to a calorie restricted diet, said low responsiveness being dependent on gut microbiota composition, said method comprising the steps of:
  (a) determining ex vivo the proportion of Lachnospiraceae in the gut (fecal) microbiota composition of a subject;
  (b) comparing the result of step (a) to a reference, preferably a reference derived from normal weight subject;
  (c) diagnosing low responsiveness to a calorie restricted diet when the result of step (a) exceeds the reference by at least 5%, more preferably by at least 10%, most preferably by at least 15%.

The object of the present invention is further solved by an agent selected from the group consisting of probiotics, preferably selected from the group consisting of probiotic *Lactobacillus rhamnosus* strains, most preferably *Lactoba-*

*cillus rhamnosus* strain CGMCC 1.3724, also referred to as *Lactobacillus rhamnosus* strain NCC4007, for use in the treatment or prevention of a disease associated with an elevated proportion of Lachnospiraceae in the gut microbiota composition of a subject.

The object of the present invention is further solved by use of an agent selected from the group consisting of probiotics, preferably selected from the group consisting of probiotic *Lactobacillus rhamnosus* strains, most preferably *Lactobacillus rhamnosus* strain CGMCC 1.3724, also referred to as *Lactobacillus rhamnosus* strain NCC4007, for the preparation of a pharmaceutical composition for the treatment or prevention of a disease associated with an elevated proportion of Lachnospiraceae in the gut microbiota compositon of a subject.

The object of the present invention is further solved by a method for treating or preventing a disease associated with an elevated proportion of Lachnospiraceae in the gut microbiota composition of a subject, the method comprising administering to the subject an effective amount of an agent selected from the group consisting of probiotics, preferably selected from the group consisting of probiotic *Lactobacillus rhamnosus* strains, most preferably *Lactobacillus rhamnosus* strain CGMCC 1.3724, also referred to as *Lactobacillus rhamnosus* strain NCC4007.

DETAILED DESCRIPTION OF THE INVENTION

The present invention elaborates the idea of controlling, manipulating, modifying or otherwise influencing the gut microbiota composition of a subject. One important aspect of this idea is the impact the gut microbiota composition may have on a subject's body weight and health condition.

In particular, the present invention is based on the finding that the relative abundance of Lachnospiraceae in the gut microbiota of a subject is associated with the subject's body weight (see Example 2; FIG. 2), and that reducing said proportion, e.g. when consuming a *Lactobacillus rhamnosus* strain, is associated with a more pronounced body weight loss (see Example 1; FIG. 1). This finding was surprising in view of the fact that Lachnospiraceae is only a small part of bacteria from the *Firmicutes* phylum, and that a decrease in the abundance of *Firmicutes* does not necessarily mean that also the abundance of Lachnospiraceae is decreased.

An association between the relative abundance of Lachnospiraceae in the gut microbiota of a subject and the subject's body weight was observed during a calorie restricted diet, i.e. during a weight loss period, where the consumption of *Lactobacillus rhamnosus* CGMCC 1.3724 enhanced the body weight loss due to restricted calorie intake (see FIG. 1 and FIG. 3, weeks 0 to 12). Remarkably, however, this effect sustained during a subsequent period without calorie restriction, i.e. during a weight maintenance period, during which *Lactobacillus rhamnosus* CGMCC 1.3724 consumption was continued (see FIG. 1, weeks 12 to 24, and FIG. 3).

As used herein including the claims, the term "agent capable of reducing the proportion of Lachnospiraceae in the gut microbiota composition of a subject" refers, for example, to a living agent such as a microbial cell, a biological agent, a chemical agent such as a small molecular compound, or a physical agent. Particularly preferred is an agent that is not absorbed through the body of a subject to which the agent is administered, as may be the case for a microbial cell.

Preferably, the agent is selected from the group consisting of food grade bacteria, preferably probiotics. However, bacterial phages, prebiotics, yeasts, antibiotics, and phytochemicals, in particular phytonutrients, are also considered. Of course, different types of agents may be combined, e.g. in a mixture or in a combination regimen.

"Food grade bacteria" means bacteria that are used and generally regarded as safe for use in food.

"Probiotics" means microbial cell preparations or components of microbial cells with a beneficial effect on the health or well-being of the host (Salminen S, Ouwehand A. Benno Y. et al "Probiotics: How should they be defined" Trends Food Sci. Technol. 1999:10 107-10).

Food grade bacteria are preferably probiotic bacteria and may be selected from the group consisting of *Bifidobacterium, Lactobacillus, Lactococcus, Enterococcus, Streptococcus Ascomycota, Deuteromycota, Debaryomyces, Kluyveromyces, Saccharomyces, Yarrowia, Zygosaccharomyces, Candida*, and *Rhodotorula*; preferentially lactic acid bacteria and bifidobacteria, or mixtures thereof; and/or in particular may be selected from the group consisting of *Bifidobacterium longum, Bifidobacterium lactis, Bifidobacterium animalis, Bifidobacterium breve, Bifidobacterium infantis, Lactobacillus acidophilus, Lactobacillus casei, Lactobacillus salivarius, Lactococcus lactis, Lactobacillus reuteri, Lactobacillus rhamnosus, Lactobacillus paracasei, Lactobacillus johnsonii, Lactobacillus plantarum, Lactobacillus salivarius, Enterococcus faecium, Saccharomyces cerevisia, Saccharomyces boulardii* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium lactis* (NCC2818; CNCM I-3446), *Lactobacillus paracasei* (NCC2461; CNCM I-2116), *Lactobacillus rhamnosus* (GG; ATCC53103), *Lactobacillus rhamnosus* (NCC4007; CGMCC 1.3724), *Enterococcus faecium* (SF 68; NCIMB10415), and mixtures thereof.

*Lactobacillus johnsonii* NCC533 was deposited on 30 Jun. 1992 with the CNCM, has received accession number CNCM I-1225. *Bifidobacterium longum* NCC490 was deposited on 15 Mar. 1999 with the CNCM, has received accession number CNCM I-2170. *Bifidobacterium longum* NCC2705 was deposited on 29 Jan. 2001 with the CNCM, has received accession number CNCM I-2618. *Bifidobacterium lactis* NCC2818 was deposited on 7 Jun. 2005 with the CNCM, has received accession number CNCM I-3446. *Lactobacillus paracasei* NCC2461 was deposited on 12 Jan. 1999 with the CNCM, has received accession number CNCM I-2116. CNCM refers to the Collection nationale de cultures de micro-organismes (CNCM), Institut Pasteur, 28, rue du Dr Roux, F-75724 Paris Cedex 15, France. *Lactobacillus rhamnosus* NCC4007, was deposited in October 2004, with the China General Microbiological Culture Collection Center (CGMCC), Institute of Microbiology, Chinese Academy of Sciences, No. 1, West Beichen Road, Chaoyang District, Beijing 100101, China, and has received accession number CGMCC 1.3724. Both CNCM and CGMCC are depositary institutions having acquired the status of international depositary authority under the Budapest Treaty on the International Recognition of the Deposit of Microorganisms for the Purposes of Patent Procedure.

The wording "reducing the proportion of Lachnospiraceae in the gut microbiota composition of a subject" refers to any reduction of the relative abundance of Lachnospiraceae in the gut or, in other words, of the abundance of Lachnospiraceae in relation to other kinds of bacteria present in the gut. As the case may be, the reduction of the proportion of Lachnospiraceae may result from an absolute or overall reduction of the abundance of Lachnospiraceae in the gut.

In this respect, "the proportion of Lachnospiraceae in the gut microbiota composition of a subject" is calculated on the basis of results from a measurement of the composition of bacteria community in the gut which, according to the present invention, is carried out by annotating bacterial 16S rDNA sequences to the Silva database followed by RDP-II Classifier. The skilled person would, however, be able to consider further methods, as appropriate. The proportion of Lachnospiraceae in the gut microbiota composition preferably is given as the relative abundance [%].

In accordance with this, the proportion of Lachnospiraceae in the gut microbiota composition of a subject may be reduced by 5-80%, preferably by 5-40%, even more preferred by 10-20% compared to the initial proportion of Lachnospiraceae in the gut microbiota of the subject before the administration of the agent.

"Lachnospiraceae" refers to a family of bacteria within the phylum *Firmicutes*. Another phylum is represented by "*Proteobacteria*", and just another phylum is represented by "Deferribacteres".

The phylum "*Firmicutes*" comprises bacteria of the classes Bacilli, Clostridia and Mollicutes, and the taxonomic order "Clostridiales" eventually comprises, inter alia, the family of Lachnospiraceae.

The term "subject" refers to an animal, preferably to a vertebrate, more preferably to a mammal, and most preferably to a human. In particular, a "subject" means an adult human.

"Body weight" or "weight" in the context of the present invention refers to the total body mass, for humans usually expressed in [kg]. Thus, "weight loss" means a reduction of total body mass, for example in an effort to improve health, fitness and/or appearance, and/or to ameliorate or reverse adverse effects on health. More specifically weight loss is a loss of body fat mass, end even preferably visceral fat mass. On the other hand, "weight gain" or "weight regain" means an increase in total body mass, for example an undesired weight regain after a period of intentional weight loss (also known as the Yo-Yo effect).

An "obese subject", an "overweight subject" or a "normal weight subject" as used herein including the claims is defined in terms of the subject's "body mass index" or "BMI". The "BMI" is defined as a subject's body mass [kg] divided by the square of height [$m^2$]. An "obese subject" is defined as an adult human having a BMI of 30 and above. In more detail, obesity class I (moderately obese) is linked to a BMI from 30 to 35, obesity class II (severely obese) is linked to a BMI from 35 to 40, and obesity class III (very severely obese) is linked to a BMI above 40. In general, "obesity" is a condition in which the natural energy reserve stored in the fatty tissue of humans and other mammals is increased to a point where it is associated with certain health conditions and adverse effects on health, respectively, and even increased mortality. An "overweight subject" is defined as an adult human having a BMI from 25 to 30. A "normal weight subject" is defined as an adult human having a BMI from 18.5 to 25. The intention of a normal weight subject to lose body weight may be, for example, in preparation of a sporting activity.

"Weight management" or "weight maintenance" relates to maintaining a total body weight. and more preferably maintenance of fat and lean body mass. For example, weight management may relate to maintaining a BMI in the area of 18.5 to 25 which is considered normal.

As nowadays weight management is no longer a problem that only concerns the adult population, the term "subject" also considers infants, children and adolescents.

Moreover, the term "subject" further considers non-human animals, preferably non-human vertebrates, more preferably non-human mammals. Particularly considered are companion animals such as pets or livestock. Animals may be selected from the group consisting of dogs, cats, pigs, cattle, horses, goats, sheep, or poultry.

The wording "for promoting weight loss" in connection with "an agent capable of reducing the proportion of Lachnospiraceae in the gut microbiota composition of a subject" means that any weight loss is more pronounced or enhanced under the agent's influence. For example, weight loss associated with a calorie restricted diet is enhanced when the agent is consumed during, subsequent to and/or prior to the diet. More preferably, a loss of body fat mass associated with a calorie restricted diet is enhanced when the agent is consumed during, subsequent to and/or prior to the diet.

The term "calorie restricted diet" refers to a dietary regimen based on a reduced calorie intake, which, for example, may be lower than a subject's previous intake, i.e. before intentionally restricting calories. A reduction of daily calorie intake by about 500 kcal usually is regarded as a "moderate calorie restriction" or "moderate energy restriction".

The wording "subsequent to a calorie restricted diet" or "prior to a calorie restricted diet" includes both the situation where a period of calorie restriction is directly linked to an otherwise characterized period of time, as well as the situation where a period of calorie restriction and an otherwise characterized period of time are interrupted by, e.g. at least one day or a couple of days.

A "low responsiveness to a calorie restricted diet, said low responsiveness being dependent on gut microbiota composition" intends to focus on the role gut bacteria play in weight management in contrast to, for example, disorders in energy metabolism such as thyroid hypofunction.

The agent according to the present invention is particular beneficial for long term application. Consequently, a preparation comprising the agent may be administered for at least 2 weeks, at least 3 weeks, at least 4 weeks, at least 5 weeks, at least 6 weeks, at least 7 weeks, and/or at least 8 weeks.

This effect may persist at least 3 days, preferably at least a week, more preferably at least 2 weeks, even more preferred at least 4 weeks, most preferred at least 5 weeks after administration of a preparation comprising the agent is discontinued.

The agent capable of reducing the proportion of Lachnospiraceae in the gut microbiota composition of a subject preferably is processed in the form of a preparation or composition. Such preparation comprising the agent may be a pharmaceutical composition or medicament. As a medicament usually requires supervision by medical personnel, a medicament has the advantage that successful administration of the agent to a subject can be carefully monitored and—if necessary—can be custom fitted to the needs of the patient to be treated.

In case of a pharmaceutical composition or a medicament, the preparation may further comprise a pharmaceutically acceptable carrier. Applicable pharmaceutically acceptable carriers are known to those of skill in the art. The pharmaceutically acceptable carrier may be any carrier known in the field as suitable for pharmaceutical and/or oral application. Suitable pharmaceutical carriers and formulations may include sugars and starches. Additional examples of pharmaceutically acceptable carriers are described, for example, in Remington's Pharmaceutical Sciences (19th ed.) (Genarro, ed. (1995) Mack Publishing Co., Easton, Pa.), the content of which is herewith incorporated herein by reference. The addition of a carrier may have the advantage that the agent capable of reducing the proportion of Lachnospiraceae in the gut microbiota of a subject is further stabilized for long storage times. Moreover, exact dosing is facilitated.

A pharmaceutical composition or a medicament may also be formulated as sustained release formulation. In this way an increased bioavailability and effectiveness of the agent capable of reducing the proportion of Lachnospiraceae in the gut microbiota of a subject can be achieved.

Alternatively, the preparation comprising the agent capable of reducing the proportion of Lachnospiraceae in the gut microbiota composition of a subject may be a food product. Food products have the advantage that the benefits of the present invention would be available to everybody immediately without requiring a medical prescription. The treatment or prevention of metabolic disorders could be initiated at a much earlier stage. Furthermore, in a food product the preparation comprising the agent according to the present invention would be even more pleasant to consume.

Generally, the dosage of the agent capable of reducing the proportion of Lachnospiraceae in the gut microbiota composition in a subject can be adjusted by those skilled in the art to the designated purpose. Any dose showing an effect is suitable. However, e.g., for probiotic bacteria it is preferred that a preparation to be administered comprises between $10^2$ and $10^{12}$ cells of probiotic per g of the dry weight of the preparation. Importantly, for the effectiveness of the agent capable of reducing the proportion of Lachnospiraceae in the gut microbiota composition it is not necessarily required that the probiotic bacteria are alive in the preparation. The probiotics might also be effective, e.g., by means of their metabolites that they have produced. Using inactive probiotics has the advantage that the amount of active agent can be exactly determined. Furthermore, inactive probiotics are usually very storage stable and easy to incorporate in products.

Nevertheless, it is preferred if the probiotics are alive, since in this case they may be able to colonize the intestine and increase their effectiveness through colonization. Consequently, in a preferred embodiment of the present invention the preparation comprises between $10^2$ and $10^{12}$ cfu of probiotic per g of the dry weight of the preparation.

If the preparation that is prepared by the use of the present invention is a liquid, in particular a drink, the given amounts should be understood as per g of the final product instead of per g of dry weight.

The daily dose of probiotics in the preparation will depend on the particular person or animal to whom or which the preparation is to be administered. Important factors to be considered include age, body weight, sex and health condition. For example a typical daily dose of probiotic in the preparation will be in the range of $10^2$-$10^{12}$ cfu and/or cells per day, preferably $10^6$-$10^{10}$ cfu and/or cells per day, preferably $10^7$-$10^9$ cfu and/or cells per day.

The agent capable of reducing the proportion of Lachnospiraceae in the gut microbiota may be provided in the form of a food product. Typical food products that may be prepared in the framework of the present invention may be selected from the group consisting of milk-powder based products; instant drinks; ready-to-drink formulations; nutritional powders; milk-based products, in particular yoghurts or ice cream; cereal products; beverages; water; coffee; cappuccino; malt drinks; chocolate flavoured drinks; culinary products and soups.

The food product preparation may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The preparation may be a nutritionally complete formula.

The preparation according to the invention may comprise a source of protein.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

The proteins may be intact or hydrolysed or a mixture of intact and hydrolysed proteins. It may be desirable to supply partially hydrolysed proteins (degree of hydrolysis between 2 and 20%), for example for animals believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The preparation may also contain a source of carbohydrates and a source of fat.

If the preparation includes a fat source, the fat source preferably provides 5% to 40% of the energy of the composition; for example 20% to 30% of the energy. A suitable fat profile may be obtained using a blend of canola oil, corn oil and high-oleic acid sunflower oil.

A source of carbohydrate may be added to the preparation.

The source of carbohydrates preferably provides 40% to 80% of the energy of the composition. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. A preferred fibre blend is a mixture of inulin with shorter chain fructo-oligosaccharides. Preferably, if fibre is present, the fibre content is between 2 and 40 g/l of the composition as consumed, more preferably between 4 and 10 g/l.

The preparation may also contain minerals and micronutrients such as trace elements and vitamins in accordance with the recommendations of Government bodies such as the US FDA. For example, the preparation may contain per daily dose one or more of the following micronutrients in the ranges given:—300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

One or more food grade emulsifiers may be incorporated into the preparation if desired; for example diacetyl tartaric acid esters of mono- and di-glycerides, lecithin and mono- and di-glycerides. Similarly suitable salts and stabilisers may be included.

The preparation is preferably orally or enterally administrable; for example in the form of a powder for re-constitution with milk or water.

Preferably, the preparation is provided in the form of a powder, e.g., a shelf stable powder. Shelf stability can be obtained, for example by providing the composition with a water activity smaller than 0.2, for example in the range of 0.19-0.05, preferably smaller than 0.15.

Water activity or $a_w$ is a measurement of the energy status of the water in a system. It is defined as the vapor pressure of water divided by that of pure water at the same temperature; therefore, pure distilled water has a water activity of exactly one.

The preparation may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

For example then the agent capable of reducing the proportion of Lachnospiraceae in the gut microbiota composition may be added in appropriate amounts. Depending on the kind of agent, it may also be added at an earlier stage.

It is clear to those skilled in the art that they can freely combine features described in this disclosure without departing from the scope of the invention as originally disclosed.

Further advantages and features of the present invention will be apparent to those of skill in the art from the following examples and figures.

EXAMPLES

Example 1

*Lactobacillus rhamnosus* CGMCC 1.3724 Promotes Body Weight Loss and Reduces the Proportion of Lachnospiraceae in Gut Microbiota Composition The effects of *Lactobacillus rhamnosus* CGMCC 1.3724 consumption on body weight and gut microbiota composition were tested in healthy adult volunteers (women).

Figure 3:
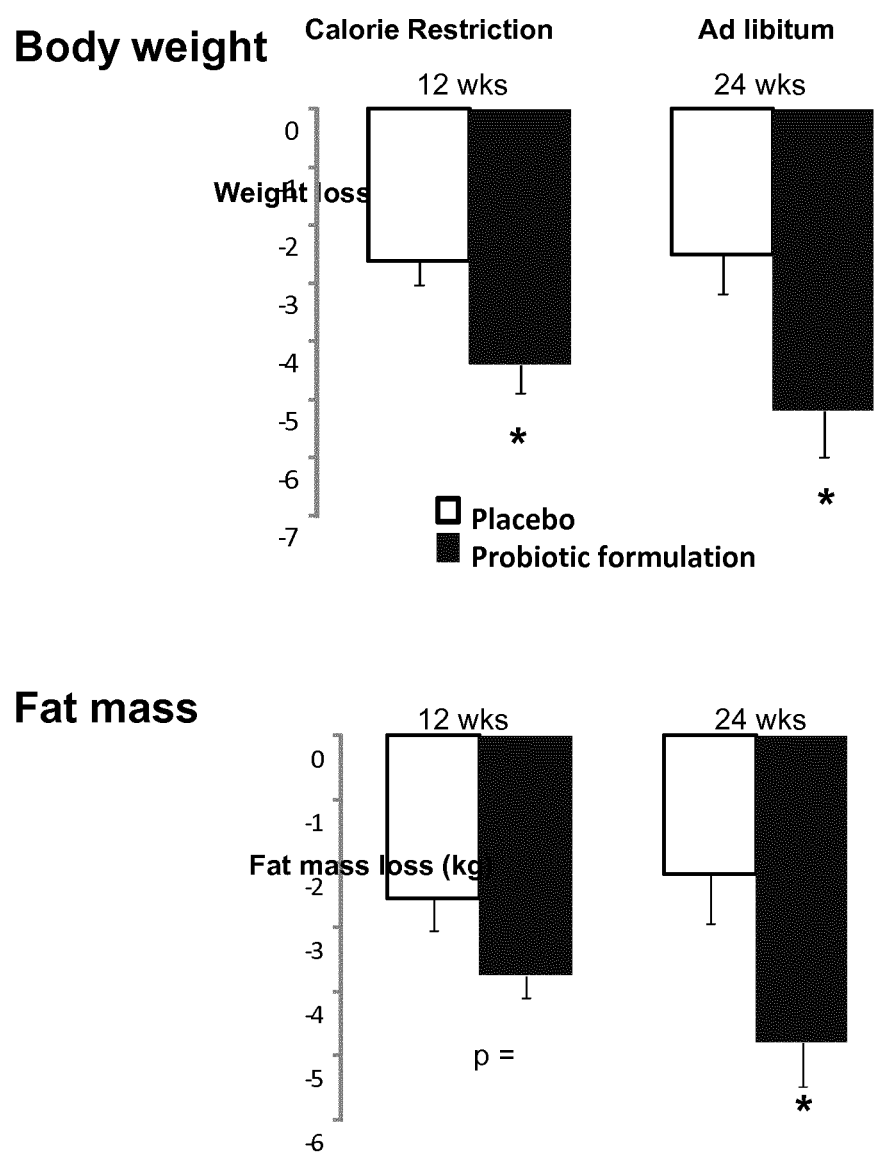
FIG. 3 shows weight and fat mass loss at 12 weeks and 24 weeks, in the placebo or probiotic group, in the placebo or probiotic group, It also shows that weight loss is essentially due to fat mass loss.

During the double blind, placebo-controlled, randomized trial each subject consumed 2 capsules per day of either a placebo (310 mg of maltodextrin) or a probiotic formulation (10 mg of (*Lactobacillus rhamnosus* CGMCC 1.3724; 1.6 $10^8$ cfu/capsule, 210 mg of oligofructose and 90 mg of inulin). Both groups were submitted to a moderate energy restriction (−500 kcal/day) for the first 12 weeks (weight loss period) followed by 12 weeks of weight maintenance. Body weight and gut microbiota composition (pyrosequencing of 16S RNAs) were measured at baseline, 12 and 24 weeks. After the first 12 weeks, mean weight loss for women in the probiotic group was significantly higher than for those in the placebo group (−4.4±3.0 vs −2.6±2.3 kg; p=0.02, respectively), and this effect was sustained after the weight maintenance period (−2.5±3.5 vs −5.2±4.0 kg; p=0.02, respectively). This is shown in FIG. 3

Figure 1:
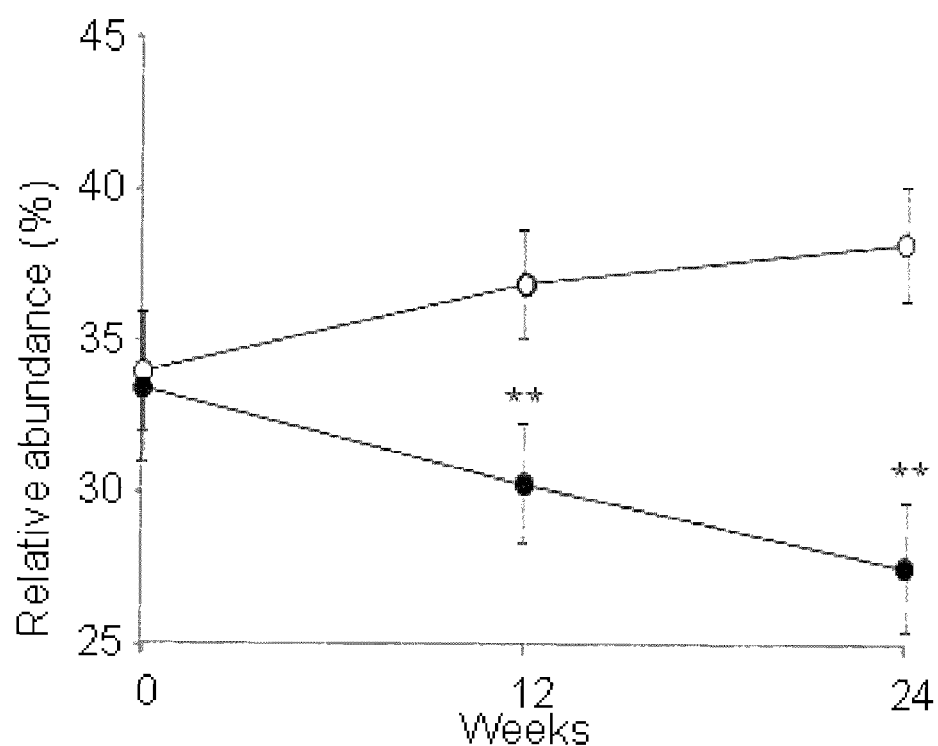
FIG. 1 shows the development of the relative abundance (%) of Lachnospiraceae family in women at week 0, week 12 and week 24 in the placebo (white circle) or the probiotic group (black circle). Data represent median±SE median. Values statistically different from placebo are indicated as **: $p<0.01$.

Furthermore, gut microbiota composition analysis revealed a significant decrease in Lachnospiraceae proportion (by 15% when compared with baseline level) associated with weight loss in women consuming the probiotic formulation (FIG. 1).

It was thus concluded that consumption of *Lactobacillus rhamnosus* CGMCC 1.3724 supports weight loss, in particular when consumed during a moderate calorie restricted diet, and that said weight loss is associated with reduction in Lachnospiraceae proportion in gut microbiota.

Example 2

Figure 2:
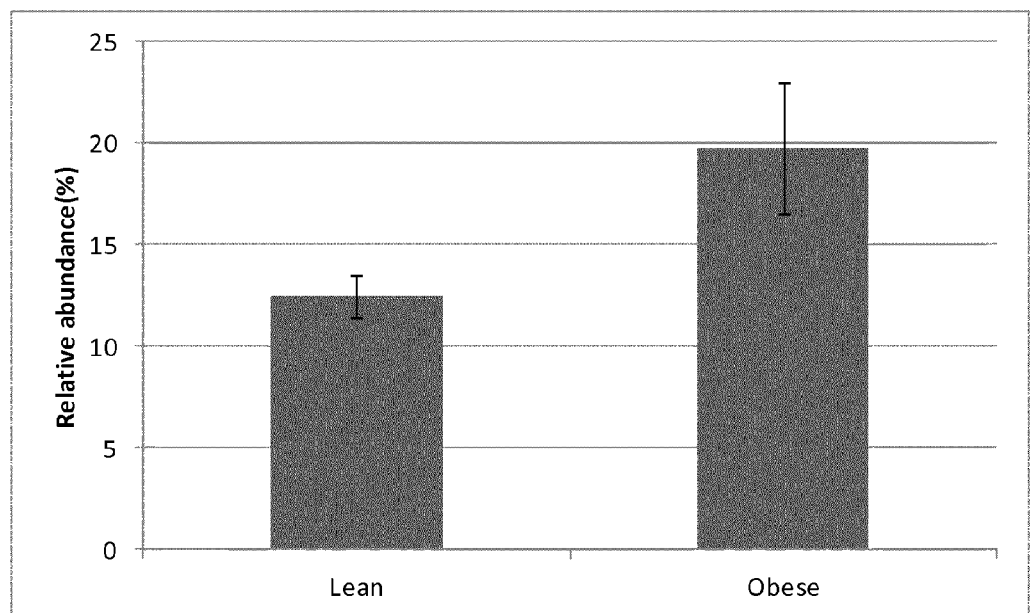
FIG. 2 shows the relative abundance (%) of Lachnospiraceae family in lean and obese subjects. Data represent median±SE median. The difference is statistically significant at $p=0.03$

Lachnospiraceae Proportion in Gut Microbiota Composition is Related to Body Weight and Obesity Fecal samples were collected from two groups of adult individuals: 20 lean non diabetic subjects (BMI: 22.3+/−1.8 kg/cm$^2$) and 25 obese non diabetic subjects (BMI: 31.5+/−4.8 kg/cm$^2$) who both followed balanced typical Western diets 14 days before fecal collection. Subjects were matched by gender and ethnic background in both groups. Fecal microbiota composition was measured by pyrosequencing of variable regions (V1 and V2) of the 16S RNA genes present in the microbial population. We showed a significantly higher proportion of Lachnospiraceae (+7%) associated with the group of obese subjects (FIG. 2).

It was thus concluded that obesity in humans is associated with a higher abundance of fecal Lachnospiraceae.

The invention claimed is:

1. A method for promoting weight loss or preventing weight gain in an obese or overweight subject having low responsiveness to a calorie restricted diet, the low responsiveness dependent on gut microbiota composition of the obese or overweight subject, the gut microbiota composition of the obese or overweight subject who has low responsiveness to the calorie restricted diet comprises a higher proportion of Lachnospiraceae relative to that of a normal weight subject, the method comprising the step of administering an agent comprising a probiotic comprising *Lactobacillus rhamnosus* CGMCC 1.3724 to the subject.

2. The method according to claim 1, wherein the agent is administered during, subsequent to and/or prior to the calorie restricted diet, in an amount therapeutically effective for promoting weight loss in the obese or overweight subject having low responsiveness to the calorie restricted diet.

3. The method according to claim 1, wherein the agent is administered subsequent to the calorie restricted diet, in an amount therapeutically effective for preventing weight gain in the obese or overweight subject having low responsiveness to the calorie restricted diet.

4. The method according to claim 1, wherein the calorie restricted diet is a dietary regimen for at least twelve weeks, and the agent is administered during the calorie restricted diet and also during a subsequent period without calorie restriction for at least twelve additional weeks.

5. The method according to claim 1, wherein the weight loss involves a body fat loss, or the weight gain involves a body fat gain.

6. The method according to claim 1, wherein the *Lactobacillus rhamnosus* CGMCC 1.3724 is administered to the subject at a daily dosage in the range of $10^2$ to $10^{12}$ cfu.

7. The method according to claim 1, wherein the agent is administered to the subject during, subsequent to and/or prior to the calorie restricted diet, the calorie restricted diet involves a reduction of the daily calorie intake in the range of 200 to 1000 kcal.

8. The method according to claim 1, wherein the proportion of Lachnospiraceae in the gut microbiota composition of the obese or overweight subject who has the low responsiveness to the calorie restricted diet exceeds that of a normal weight subject by at least 5%.

9. The method according to claim 1, wherein the proportion of Lachnospiraceae in the gut microbiota composition of the obese or overweight subject who has the low responsiveness to the calorie restricted diet exceeds that of a normal weight subject by at least 10%.

10. The method according to claim 1, wherein the proportion of Lachnospiraceae in the gut microbiota composition of the obese or overweight subject who has the low responsiveness to the calorie restricted diet exceeds that of a normal weight subject by at least 15%.

11. The method according to claim 1, wherein the agent is administered to the subject for a period of time of greater than 12 weeks.

* * * * *